United States Patent
Basset et al.

(10) Patent No.: US 7,378,564 B2
(45) Date of Patent: May 27, 2008

(54) PROCESS FOR MANUFACTURING ALKANES BY REACTING OTHER ALKANES WITH METHANE

(76) Inventors: Jean-Marie Basset, 18 Chemin J.B. Gilliard, 69300 Caluire (FR); Christophe Coperet, 136 Avenue Thiers, 69006 Lyon (FR); Richard Pardy, 99 The Meadows, Cherry Burton, Near Beverley, East Yorkshire, HU17 7RL (GB); Daravong Soulivong, 8 rue Turbil, 69003 Lyon (FR); John Glenn Sunley, 7 Hall Walk, Cottingham, East Yorkshire, HU16 4RL (GB); Jean Thivolle-Cazat, 5 rue Gambetta, 69270 Fontaines-sur-Saone (FR)

(*) Notice: Subject to any disclaimer, the term of this patent is extended or adjusted under 35 U.S.C. 154(b) by 686 days.

(21) Appl. No.: 10/502,845

(22) PCT Filed: Jan. 22, 2003

(86) PCT No.: PCT/GB03/00257

§ 371 (c)(1),
(2), (4) Date: Jul. 29, 2004

(87) PCT Pub. No.: WO03/066552

PCT Pub. Date: Aug. 14, 2003

(65) Prior Publication Data

US 2005/0014987 A1    Jan. 20, 2005

(30) Foreign Application Priority Data

Feb. 6, 2002    (FR)    ................................ 02 01389

(51) Int. Cl.
*C07C 6/08*    (2006.01)
(52) U.S. Cl. ...................................... 585/709; 585/943
(58) Field of Classification Search ................ 585/708; 1/943
See application file for complete search history.

(56) References Cited

FOREIGN PATENT DOCUMENTS

WO    WO 98/02244    1/1998
WO    WO 01/04077 A1    1/2001

*Primary Examiner*—Thuan Dinh Dang
(74) *Attorney, Agent, or Firm*—Nixon & Vanderhye

(57) ABSTRACT

The present invention relates to a process for the manufacture of alkanes comprising a catalytic reaction resulting from contacting methane with at least one other starting alkane (I) in the presence of a metal compound (C) capable of catalysing a reaction for the splitting and/or recombination of a carbon-carbon bond and/or of a carbon-hydrogen bond and/or of a carbon-metal bond, which catalytic reaction results in the formation of at least one final alkane (II) having a number of carbon atoms equal to or greater than (2). In the process, the contacting operation is carried out under a methane partial pressure equal to or greater than 0.1 MPa, preferably in the range from 0.1 to 100 MPa. The metal compound (C) can be chosen from metal compounds supported on and dispersed over a solid support, metal compounds supported on and grafted to a solid support and non-supported metal compounds. Under these conditions, it was found that the yield of the catalytic reaction was improved, and that the catalytic stability and activity of the metal compound (C) over timer were greatly enhanced.

23 Claims, No Drawings

PROCESS FOR MANUFACTURING ALKANES BY REACTING OTHER ALKANES WITH METHANE

This application is the U.S. National Phase of International Application PCT/GB03/00257, filed 22 Jan. 2003, which designated the U.S.

The present invention relates to an improved process for the manufacture of alkanes by catalytic reaction employing methane with at least one other alkane.

Alkanes, such as methane, are generally products which are difficult to employ in reactions because of their high chemical inertia and are used essentially as fuels and energetic materials. Furthermore, methane is known to be one of the most widespread sources of hydrocarbons in the world.

It is already known to convert alkanes into other alkanes, for example by hydrogenolysis reactions, which consist of reactions for the splitting or opening of a carbon-carbon bond by hydrogen. Isomerization reactions which convert an alkane into one of its isomers, for example n-butane into isobutane, are also known. These reactions are generally carried out at relatively high temperatures and in the presence of catalysts based on metals, in particular on transition metals, especially dispersed or fixed to solid supports, for example to metal oxides or refractory oxides. More particularly, the catalysts can be catalysts of nickel black, $Ni/SiO_2$, platinum black, $Pt/SiO_2$ or $Pd/Al_2O_3$ type or films of tungsten or of rhodium optionally mixed with copper, tin or silver. In some cases, it has been possible to simultaneously observe reactions for the homologation of alkanes, which consist of reactions in which initial (or starting) alkanes are converted into higher homologous alkanes. However, these homologation reactions often remain very minor in comparison with the hydrogenolysis or isomerization reactions and their performances are generally very poor.

Nevertheless, it remains the case that a process for the conversion of an alkane into one of its homologues would constitute a means for enhancing in value alkanes in general and in particular methane. It is known that light alkanes and methane in particular are difficult to enhance in value in the chemical or petrochemical industry, whereas heavier alkanes often have greater commercial interest, in particular as additives intended to increase the octane number of fuels, or as starting materials in thermal or catalytic cracking reactions for manufacturing, for example, olefins or dienes.

In this sense, International Patent Application WO 01/04077 discloses a process for the manufacture of alkanes comprising a reaction resulting from bringing methane into contact with at least one other starting alkane (A) in the presence of a metal compound capable of catalysing a metathesis of alkanes. The reaction results in the formation of at least one or two final alkanes (B) having a number of carbon atoms lower than or equal to that of the starting alkane (A) and at least equal to 2, for example according to the following equation.

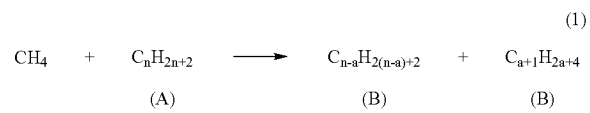

(1)

in which n is an integer at least equal to 2 and a is an integer ranging from 1 to n−1.

It is specified in particular that the reaction can be carried out at a temperature ranging from −30 to +400° C. and under an absolute pressure which can vary within a very wide range, preferably under an absolute pressure of less than atmospheric pressure, and in particular under a methane partial pressure equal to 0.0645 MPa, as shown in the examples.

It has been observed that the process for the manufacture of alkanes described above may have certain disadvantages during its implementation. In particular, it has been noticed that, on applying a methane partial pressure of less than atmospheric pressure, the yield of the reaction resulting from bringing methane into contact with another alkane very rapidly decreases over time. The fact has also been demonstrated that, under these conditions, the metal compound used as catalyst rapidly loses its activity and is very unstable over time.

A process for the manufacture of alkanes has now been found which makes it possible to considerably improve the yield of the reaction between methane and the other starting alkane or alkanes, in particular the yield of the reaction with respect to the metal compound employed as catalyst, or, in other words, to considerably increase the overall conversion of the starting alkane or alkanes charged to the reaction with methane. In particular, reaction conditions have been found which make it possible to maintain the catalytic activity of the metal compound at a particularly high level over time and consequently to increase the overall catalytic activity of the reaction. It has thus been observed with surprise that, on carrying out this reaction under a high methane partial pressure, the metal compound used as catalyst exhibits a considerably increased catalytic stability over time, without it being possible to find an immediate explanation for this phenomenon.

A particular subject-matter of the invention is a process for the manufacture of alkanes comprising, particularly as a main stage, a catalytic reaction resulting from bringing methane into contact with at least one other starting alkane (I) in the presence of a metal compound (C) capable of catalysing a reaction for the splitting and/or recombination of a carbon-carbon bond and/or of a carbon-hydrogen bond and/or of a carbon-metal bond, which catalytic reaction results in the formation of at least one final alkane (II) having a number of carbon atoms equal to or greater than 2, which process is characterized in that the operation is carried out under a methane partial pressure equal to or greater than 0.1 MPa, preferably equal to or greater than 0.2 MPa, in particular equal to or greater than 0.3 or equal to or greater than 0.5 MPa, and which can be chosen within a range more particularly from 0.1 to 100 MPa.

The "methane-olysis" catalytic reaction, as shown by equation (1), results from bringing methane into contact with at least one other starting alkane (I) having n carbon atoms with n being equal to at least 2, preferably to at least 3, so that the catalytic reaction generally results in the formation of at least one final alkane (II) or of at least two final alkanes (II) having a number of carbon atoms ranging from 2 to (n−1) or even to a value greater than (n−1). This is because the alkane or alkanes resulting directly from the "methane-olysis" reaction can themselves participate in at least one reaction for the metathesis of other alkanes. The catalytic reaction can be written according to one or more equations (1) described above in which n is an integer at least equal to 2, preferably at least equal to 3, and a is an integer ranging from 1 to n−1 or even more. It is essentially an equilibrated catalytic reaction.

According to another aspect, another subject-matter of the invention is in particular a process for increasing the catalytic activity and stability of a metal compound (C) capable of catalysing a reaction for the splitting and/or recombination of a carbon-carbon bond and/or of a carbon-hydrogen bond and/or of a carbon-metal bond, which compound is employed, particularly as a main stage, in a catalytic reaction which results from bringing methane into contact with at least one other starting alkane (I) and which results in the formation of at least one final alkane (II) having a number of carbon atoms equal to or greater than 2, which process is characterized in that the contacting operation is carried out under a methane partial pressure equal to or greater than 0.1 MPa, preferably equal to or greater than 0.2 MPa, in particular equal to or greater than 0.3 or equal to or greater than 0.5 MPa, and which can be chosen within a range more particularly from 0.1 to 100 MPa.

It is particularly surprising to find that the application of a high methane partial pressure in such a process has so great an effect on the catalytic stability of the metal compound (C) when the latter is used in "methane-olysis" reactions between methane and at least one other alkane.

According to the invention, the methane partial pressure applied when methane is brought into contact with at least one other starting alkane (I) can be from 0.1 to 100 MPa, preferably from 0.1 to 50 MPa, in particular from 0.1 to 30 MPa or from 0.2 to 20 MPa, especially from 0.3 to less than 10 MPa, for example from 0.3 to 9.5 MPa, or from 0.5 to 9.5 MPa.

The contacting operation can be carried out at a temperature ranging from −30 to +500° C., preferably from 0 to 500° C. or from 0 to 400° C., in particular from 20 to 500° C. or from 20 to 300° C. A range of temperature particularly from 50 to 500° C., preferably from 50 to 450° C., especially from 100 to 450° C. may be preferred.

The contacting operation can be carried out by adding methane or the other starting alkane or alkanes (I) to the metal compound (C), either separately and in any order, or simultaneously with at least two separate introductions, or mixed beforehand and using, in this case, a single introduction.

Methane and the starting alkane or alkanes (I) can be employed in a molar ratio of methane to the starting alkane or alkanes (I) ranging from 0.1:1 to $10^5$:1, preferably from 1:1 to $10^4$:1, in particular from 1:1 to $5 \times 10^3$:1, for example from 1:1 to $3 \times 10^3$:1. During the contacting operation, it is particularly advantageous to employ a molar amount of methane greater than or even much greater than the molar amount of the other starting alkane or alkanes (I). Thus, for example, the methane starting alkane(s) (I) molar ratio can range from 60:1 to $10^5$:1, preferably from 60:1 to $10^4$:1, in particular from 60:1 to $5 \times 10^3$:1.

In a "methane-olysis" reaction carried out in particular batchwise, the metal compound (C) can be employed when methane is brought into contact with the other starting alkane or alkanes (I) in a molar ratio of methane to the metal of the metal compound (C) ranging from 10:1 to $10^5$:1, preferably from 50:1 to $10^4$:1, in particular from 50:1 to $10^3$:1.

The contacting operation can be carried out in the presence of one or more liquid or gaseous inert agents, in particular inert gases, such as nitrogen, helium or argon.

The process for the manufacture of alkanes resulting from the contacting operation according to the invention can be carried out batchwise or, preferably, continuously. It can be carried out in the gas phase, in particular in a mechanically stirred and/or fluidized bed reactor or a stationary or circulating bed reactor, the bed being composed essentially of the metal compound (C), for example a metal compound supported on and dispersed over a solid support, or a metal compound supported on and grafted to a solid support, or a non-supported metal compound in the form of a solid. The process can also be carried out in the liquid phase preferably being composed essentially of the starting alkane or alkanes (I) in the liquid state, under the conditions of the catalytic reaction. The metal compound (C) can in particular be suspended in the liquid phase, in particular when the metal compound (C) is a metal compound supported on and dispersed over a solid support or a metal compound supported on and grafted to a solid support, or a non-supported solid metal compound. It is preferable to carry out the process continuously, either in the gas phase or in the liquid phase, in a reaction region into which methane and the starting alkane or alkanes (I) are introduced continuously and where they come into contact with the metal compound (C) present in the said region, the products resulting from the contacting operation being withdrawn continuously from the region in order to be partially or completely separated from the starting materials introduced and optionally to be recycled to the region.

The contacting operation of the process according to the invention comprises the use of methane with at least one starting alkane (I) which can be a substituted or unsubstituted acyclic alkane, that is to say composed of a linear or branched, but unclosed, carbonaceous chain. It can correspond to the general formula:

$$C_nH_{2n+2} \qquad (2)$$

in which n is an integer ranging from 2 to 60 or from 3 to 60, preferably from 3 to 50, in particular from 3 to 20.

The starting alkane (I) can also be a substituted (or branched) cyclic alkane, that is to say composed of a branched and closed carbonaceous chain. The substituted cyclic alkane comprises at least one substitution (or branching) itself composed in particular of a linear or branched carbonaceous chain, for example of an alkyl chain. It can correspond to the general formula:

$$C_nH_{2n} \qquad (3)$$

in which n is an integer ranging from 5 to 60, preferably from 5 to 20, in particular from 5 to 10.

More particularly, the starting alkane (I) can be chosen from linear or branched $C_3$ to $C_{10}$ or $C_3$ to $C_{17}$ alkanes, for example from propane, n-butane, isobutane, n-pentane, isopentane, n-hexane, n-heptane, n-octane, n-nonoane and n-decane.

Thus, for example, in the process of the present invention, methane can be brought into contact with propane, and ethane or possibly other higher alkanes can be formed; or else methane can be brought into contact with n-butane, and ethane, or in particular a mixture of ethane and of propane, and possibly other higher alkanes resulting from other "methane-olysis" and/or metathesis reactions, in particular of the ethane formed and/or of the propane formed, can be formed.

The starting alkane (I) can also be chosen from paraffins, such as n-paraffins, isoparaffins and cycloparaffins, for example linear, branched or cyclic $C_{18}$ to $C_{60}$ or $C_{22}$ to $C_{60}$ or $C_{18}$ to $C_{45}$ alkanes.

The process of the present invention can be carried out by contacting methane with one or more starting alkanes (I), that is to say a mixture of two or more starting alkanes (I), such as those described above. When one starting alkane (I) is used with methane, the process resulting from such a contacting generally involves an alkane "methane-olysis" reaction simultaneously with an alkane self-metathesis reaction. When two or more starting alkanes (I) are used with methane, the process resulting from such a contacting may involve alkane "methane-olysis" reactions simultaneously with some alkane metathesis reactions and alkane self-metathesis reactions.

Methane is brought into contact with at least one starting alkane (I) in the presence of a metal compound (C) which is capable of catalysing a reaction for the splitting and/or recombination of a carbon-carbon bond and/or of a carbon-hydrogen bond and/or of a carbon-metal bond. The metal compound (C) can be chosen from metal compounds supported on and dispersed over a solid support, metal compounds supported on and grafted to a solid support, and non-supported metal compounds.

The term "metal compound" is understood to mean generally both a metal and a chemical compound comprising a metal, that is to say a metal bonded chemically to at least one other element.

The term "metal compound (or atom) grafted to a solid support" is understood to mean generally a metal compound (or atom) which is (chemically) fixed to the support, in particular by at least one single or multiple bond, and which in particular is bonded directly to at least one of the essential elements (or constituents) of the solid support.

The Periodic Table of the Elements cited below is that proposed by the IUPAC in 1991 and which is found, for example, in "CRC Handbook of Chemistry and Physics", 76th Edition (1995-1996), by David R. Lide, published by CRC Press, Inc. (USA).

The metal atom, Me, present in the metal compound (C) can be at least one metal chosen from the lanthanides, the actinides and the metals from Groups 2 to 12, preferably the transition metals from Groups 3 to 12, in particular from Groups 3 to 10, of the Periodic Table of the Elements. The metal atom, Me, can in particular be at least one metal chosen from scandium, yttrium, lanthanum, titanium, zirconium, hafnium, vanadium, niobium, tantalum, chromium, molybdenum, tungsten, ruthenium, palladium, platinum, iridium, cerium and neodymium. It can preferably be chosen from titanium, zirconium, hafnium, vanadium, niobium, tantalum, chromium, molybdenum and tungsten, and more preferably from tantalum, chromium, yttrium, vanadium, niobium, molybdenum and tungsten.

The metal compound (C) can in particular be chosen from metal compounds supported and dispersed on a solid support, that is to say metal compounds or metals supported on and dispersed over a support, such as, for example, metal particles dispersed over a support. The metal compounds supported on and dispersed over a support can comprise identical different metal atoms, Me, that is to say metal atoms which are not fixed (chemically) to the support, or, in other words, which have no connection via single or multiple bonds with the support, in particular with the essential elements of the support.

The metal compound (C) can also be chosen from metal compounds supported on and grafted to a solid support, comprising one or more identical or different metal atoms, Me, in particular fixed (chemically) to the support, especially via single or multiple bonds. The metal atoms, Me, grafted to the support can additionally be advantageously bonded to at least one hydrogen atom and/or to at least one hydrocarbon radical.

In the case where the metal atom, Me, grafted to a support is additionally bonded to at least one hydrogen atom, the metal compound (C) can be chosen from supported and grafted metal compounds comprising a solid support to which is grafted at least one metal hydride, in particular a hydride of the metal Me.

In the case where the metal atom, Me, grafted to a support is additionally bonded to at least one hydrocarbon radical, the metal compound (C) can be chosen from supported and grafted metal compounds comprising a solid support to which is grafted at least one organometallic compound, in particular an organometallic compound of the metal Me.

Thus, the metal compound (C) can advantageously be chosen from metal hydrides and/or organometallic compounds, in particular of the metal Me, supported on and grafted to a solid support.

The metal compound (C) can also advantageously be chosen from supported and grafted metal compounds comprising a solid support to which are grafted at least two types of metal atom, Me, one in a form (A) of a metal compound where the metal atom is bonded to at least one hydrogen atom and/or to at least one hydrocarbon radical, and the other in a form (B) of a metal compound where the metal atom is solely bonded to the support and optionally to at least one other component which is neither a hydrogen atom nor a hydrocarbon radical. The metal atoms, Me, can correspond to identical or different metals for each of the forms (A) or (B). The metal atoms, Me, present in the form (A) can be identical to or different from those present in the form (B). When the forms (A) and (B) coexist in the metal compound (C), the degree of oxidation of the metal atoms, Me, present in the form (A) can be identical to or different from that of the metal atoms, Me, present in the form (B).

The solid support can be any solid support, in particular essentially comprising atoms M and X which are different from one another and which are generally bonded to one another via single or multiple bonds, so as to form in particular the molecular structure of the solid support. The term "support essentially comprising atoms M and X" is understood to mean generally a support which comprises, as predominant constituents, the atoms M and X and which can additionally comprise one or more other atoms capable of modifying the structure of the support.

The atom M of the support can be at least one of the elements chosen from the lanthanides, the actinides and the elements from Groups 2 to 15 of the Periodic Table of the Elements. The atom M of the support can be identical to or different from the metal atom, Me. The atom M can be at least one of the elements chosen in particular from magnesium, titanium, zirconium, cerium, vanadium, niobium, tantalum, chromium, molybdenum, tungsten, boron, aluminium, gallium, silicon, germanium, phosphorus and bismuth. The atom M of the support is preferably at least one of the elements chosen from the lanthanides, the actinides and the elements from Groups 2 to 6 and from Groups 13 to 15 of the Periodic Table of the Elements, in particular from silicon, aluminium and phosphorus.

The atom X of the support, which is different from the atom M, can be chosen from at least one of the elements from Groups 15 and 16 of the Periodic Table of the Elements, it being possible for the element to be alone or itself optionally bonded to another atom or to a group of atoms. In the case where the atom X of the support is chosen in particular from at least one of the elements from Group 15, it can optionally be bonded to another atom or to a group of atoms chosen, for example, from a hydrogen atom, a halogen atom, in particular a fluorine, chlorine or bromine atom, a saturated or unsaturated hydrocarbon radical, a hydroxyl group of the formula (—OH), a hydrogensulphide group of formula (—SH), alkoxide groups, thiolate groups, or silylated (or silane) or organosilylated (or organosilane) groups. The atom X of the support is preferably at least one of the elements chosen from oxygen, sulphur and nitrogen and more particularly from oxygen and sulphur.

The atoms M and X which represent generally the essential elements of the solid support can in particular be bonded to one another via single or double bonds. In a preferred alternative form, the solid support can be chosen from oxides, sulphides and azides in particular of M, and the mixtures of two or three of the oxides, sulphides and/or azides. More particularly, the support can be an oxide in particular of M and can be chosen from simple or mixed oxides in particular of M, or mixtures of oxides in particular of M. The support can be, for example, chosen from metal oxides, refractory oxides and molecular sieves, in particular from silica, alumina, aluminosilicates, aluminium silicates, simple or modified by other metals, zeolites, clays, titanium oxide, cerium oxide, magnesium oxide, niobium oxide, tantalum oxide and zirconium oxide. The support can also be a metal oxide or refractory oxide, optionally modified by an acid, and optionally comprising in particular an atom M bonded to at least to atoms X which are different from one another, for example the oxygen atom and the sulphur atom. Thus, the solid support can be chosen from sulphated metal oxides or refractory oxides, for example a sulphated alumina or a sulphated zirconia. The support can also be chosen from metal sulphides or refractory sulphides and sulphided metal oxides or refractory oxides, for example a molybdenum sulphide, a tungsten sulphide or a sulphided alumina. The support can also be chosen from azides, in particular boron azide.

The essential constituents of the solid support are preferably the atoms M and X described above. In addition, the solid support has the advantage of generally exhibiting, at the surface, atoms X capable of forming part of the coordination sphere of the metal atoms, Me, of the metal compound (C), in particular when the latter is chosen from the metal compounds supported on and grafted to a solid support. Thus, at the surface of the support, the atom X which is bonded to at least one metal atom, Me, can advantageously be bonded to at least one atom M. The bonds between X and M, on the one hand, and between X and Me, on the other hand, can be single or double bonds.

In the case of a metal compound supported on and grafted to a support, the metal atom, Me, in particular present in the form (A), can be bonded, on the one hand, to the support, in particular to at least one atom constituting the support, preferably the atom X of the support as described above, and in particular via a single or double bond, and, on the other hand, to at least one hydrogen and/or to at least one hydrocarbon radical, R, in particular via a carbon-metal single, double or triple bond. The hydrocarbon radical, R, can be saturated or unsaturated, can have from 1 to 20, preferably from 1 to 10, carbon atoms and can be chosen from alkyl, alkylidene or alkylidyne radicals, in particular $C_1$ to $C_{10}$, preferably $C_1$, alkyl, alkylidene or alkylidyne radicals, aryl radicals, in particular $C_6$ to $C_{10}$ aryl radicals, and aralkyl, aralkylidene or aralkylidyne radicals, in particular $C_7$ to $C_{14}$ aralkyl, aralkylidene or aralkylidyne radicals.

In the case of a metal compound supported on and grafted to a support, the metal atom, Me, in particular present in the form (A) can be bonded to the hydrocarbon radical, R, via one or more carbon-metal single, double or triple bonds. It can be a carbon-metal single bond, in particular of the σ type: in this case, the hydrocarbon radical, R, can be an alkyl radical, in particular a linear or branched alkyl radical, for example a $C_1$ to $C_{10}$, preferably $C_1$, alkyl radical, or an aryl radical, for example the phenyl radical, or an aralkyl radical, for example the benzyl radical. The term "alkyl radical" is understood to mean generally a monovalent aliphatic radical originating from the removal of a hydrogen atom in the molecule of an alkane or of an alkene or of an alkyne, for example the methyl, ethyl, propyl, neopentyl, allyl or ethynyl radical. The methyl radical is preferred.

It can also be a carbon-metal double bond, in particular of the π type: in this case the hydrocarbon radical, R, can be alkylidene radical, in particular a linear or branched alkylidene radical, for example a $C_1$ to $C_{10}$, preferably $C_1$, alkylidene radical, or an aralkylidene radical, for example $C_7$ to $C_{14}$ aralkylidene radical. The term "alkylidene radical" is understood to mean generally a bivalent aliphatic radical originating from the removal of two hydrogen atoms on the same carbon from the molecule of an alkane or an alkene or of an alkyne, for example, the methylidene, ethylidene, propylidene, neopentylidene or allylidene radical. The methylidene radical is preferred. The term "aralkylidene radical" is understood to mean generally a bivalent aliphatic radical originating from the removal of two hydrogen atoms on the same carbon from an alkyl, alkenyl or alkynyl linking unit of an aromatic hydrocarbon.

It can also be a carbon-metal triple bond: in this case, the hydrocarbon radical, R, can be an alkylidyne radical, in particular a linear or branched alkylidine radical, for example a $C_1$ to $C_{10}$, preferably $C_1$, alkylidyne radical, or an aralkylidyne radical, for example a $C_7$ to $C_{14}$ aralkylidyne radical. The term "alkylidyne radical" is understood to mean generally a trivalent aliphatic radical originating from the removal of three hydrogen atoms on the same carbon from the molecule of an alkane or of an alkene or of an alkyne, for example the methylidyne, ethylidyne, propylidyne, neopentylidyne or allylidyne radical. The methylidyne radical is preferred. The term "aralkylidyne radical" is understood to mean generally a trivalent aliphatic radical originating from the removal of three hydrogen atoms on the same carbon from an alkyl, alkenyl or alkynyl linking unit of an aromatic hydrocarbon.

The metal compound (C) can advantageously be chosen from the metal compounds supported on and grafted to a solid support comprising the metal atom, Me, present in the two forms (A) and (B). Such a compound has the advantage of exhibiting a particularly high catalytic activity in reactions for the splitting and/or recombination of a carbon-carbon bond and/or a carbon-hydrogen bond and/or a carbon-metal bond. The form (A) of the metal compound is that described above. In the form (B), the metal atom, Me, is preferably bonded solely to the support, in particular to one or more atoms constituting the essential elements of the support, in particular to one or more atoms X of the support as described above, for example via single or double bonds.

In the form (B), the metal atom, Me, can optionally be bonded, in addition to the support, to at least one other component which is neither a hydrogen atom nor a hydrocarbon radical. The other component bonded to the metal Me can be, for example, at least one of the elements from Groups 15 to 17 of the Periodic Table of the Elements, which element can be alone or itself bonded to at least one hydrogen atom and/or to at least one hydrocarbon radical and/or to at least one silylated (or silane) or organosilylated (or organosilane) group. In particular, the metal atom, Me, present in the form (B) can optionally be bonded, in addition to the support, to at least one atom of the elements chosen from oxygen, sulphur, nitrogen and halogens, in particular flourine, chlorine or bromine. Thus, for example, the metal atom, Me, can be bonded, via a single bond, to one or more halogen atoms, in particular fluorine, chlorine or bromine. It can also be bonded, via a double bond, to one or more oxygen or sulphur atoms, in particular in the form of a metal oxide or a metal sulphide. It can also be bonded, via a single bond, to at least one oxygen or sulphur atom, itself bonded to a hydrogen atom or to a saturated or unsaturated hydrocarbon radical, in particular a $C_1$ to $C_{20}$, preferably $C_1$ to $C_{10}$, radical, for example in the form of a hydroxide, of a hydrogensulphide, of an alkoxide or of a thiolate. It can also be bonded, via a single bond, to a silylated or organosilylated group. It can also be bonded, via a single bond, to an amido (or amide) group, for example of formulae ($NH_2$—), (NHR—) or (NRR'—), in which R and R', which are identical or different, represent saturated or unsaturated hydrocarbon radicals, in particular $C_1$ to $C_{20}$, preferably $C_1$ to $C_{10}$, radicals, or silylated or organosilylated groups, or else can be bonded, via a double bond, to an imide (or imide) group, for example of formula (NH≡) or via a triple bond, to a nitride, (or azide) group for example of formula (NH≡).

It is preferable to use the metal compounds supported on and grafted to a solid support in which the metal atoms, Me, grafted to the support exist simultaneously in the two forms (A) and (B), because these metal compounds advantageously exhibit a very high catalytic activity in the splitting and/or recombination reactions described above, in particular when, per 100 mol of the metal Me grafted to the support, the metal compound comprises:

(a) from 5 to 95 mol, preferably from 10 to 90 mol, in particular from 20 to 90 mol, especially from 25 to 90 mol, or more particularly from 30 to 90 mol, of the metal Me in the form (A), and (b) from 95 to 5 mol, preferably from 90 to 10 mol, in particular from 80 to 10 mol, especially from 75 to 10 mol, or more particularly, from 70 to 10 mol, of the metal Me in the form (B).

The metal compound (C) can also be chosen from the non-supported metal compounds, that is to say non-supported metal compounds or non-supported metals, which can in particular be provided in any solid form, preferably in the form of films or of particles.

The metal compounds (C) described above can be prepared in various ways. A first process for the preparation of a metal compound supported on and grafted to a solid support can comprise the following stages:

(a) grafting an organometallic precursor (P) comprising the metal Me, bonded to at least one hydrocarbon ligand, to the solid support, and (b) treating the solid product resulting from stage (a) with hydrogen or a reducing agent capable of forming a metal Me-hydrogen bond, preferably by hydrogenolysis of the hydrocarbon ligands, at a temperature in particular at most equal to the temperature T1 at which the metal compound is formed solely in the form (A) as defined above.

The temperature of stage (b) is chosen in particular so that it is at most equal to the temperature T1 where only the form (A) of the metal compound is formed, that is to say where only the metal hydride is formed. The temperature of stage (b) can in particular be chosen within the range from 50 to 160° C., preferably from 100 to 150° C. Stage (b) can take place under an absolute pressure of $10^{-3}$ to 10 MPa and for a period of time which can range from 1 to 24 hours, preferably from 5 to 20 hours.

A second process for the preparation of a metal compound supported on and grafted to a solid support can comprise the following stages:

(a) grafting an organometallic precursor (P) comprising the metal Me, bonded to at least one hydrocarbon ligand, to the solid support, and (b) treating the solid product resulting from stage (a) with hydrogen or a reducing agent capable of forming a metal Me-hydrogen bond, preferably by hydrogenolysis of the hydrocarbon ligands, at a temperature greater than the temperature T1 at which the metal compound is formed solely in the form (A), and lower than the temperature T2 at which the metal compound is formed solely in the form (B), the forms (A) and (B) being those described above.

The temperature of stage (b) is chosen in particular so that it is greater than the temperature T1 where only the form (A) is formed. It can in particular be at least 10° C., preferably at least 20° C., in particular at least 30° C. or even at least 50° C., greater than the temperature T1. In addition, it is chosen in particular so that it is lower than the temperature T2 where only the form (B) is formed. It can in particular be at least 10° C., preferably at least 20° C., in particular at least 30° C. or even at least 50° C., lower than the temperature T2. The temperature of stage (b) can, for example, be chosen within the range from 165° C. to 450° C., preferably from 170 to 430° C., in particular from 180 to 390° C., especially from 190 to 350° C. or from 200 to 320° C. Stage (b) can take place under an absolute pressure of $10^{-3}$ to 10 MPa, and for a period of time which can range from 1 to 24 hours, preferably from 5 to 20 hours.

A third process for the preparation of a metal compound supported on and grafted to a solid support can comprise the following stages:

(a) grafting an organometallic precursor (P) comprising the metal Me, bonded to at least one hydrocarbon ligand, to a solid support, then (b) treating the solid product resulting from stage (a) with hydrogen or a reducing agent capable of forming a metal Me-hydrogen bond, preferably by complete hydrogenolysis of the hydrocarbon ligands, at a temperature in particular at most equal to the temperature T1 at which the metal compound is formed solely in the form (A) as defined above, so as to form a metal hydride in the form (A), and (c) heat-treating the solid, product resulting from stage (b), preferably in the presence of hydrogen or of a reducing agent, at a temperature greater than the temperature of stage (b) and lower than the temperature T2 at which the metal compound is formed solely in the form (B) as defined above.

Stage (b) of the process can be carried out under the same conditions, in particular of temperature, as those of stage (b) of the first preparation process. Stage (c) can be carried out at a temperature, under a pressure and for a period of time equivalent to those described in stage (b) of the second preparation process.

A fourth process for the preparation of a metal compound supported on and grafted to a solid support can comprise the following stages:

(a) grafting an organometallic precursor (P) comprising the metal Me, bonded to at least one hydrocarbon ligand, to the solid support comprising functional groups capable of grafting the precursor (P), by bringing the precursor (P) into contact with the solid support, so as to graft the precursor (P) to the support by reaction of (P) with a portion of the functional groups of the support, preferably from 5 to 95% of the functional groups of the support, then (b) heat-treating the solid product resulting from stage (a), preferably in the presence of hydrogen or of a reducing agent, at a temperature equal to or greater than the temperature T2 at which the metal compound is formed solely in the form (B) as defined above, then (c) grafting, to the solid product resulting from stage (b), an organometallic precursor (P'), identical to or different from (P), comprising the metal Me, bonded to at least one hydrocarbon ligand, the metal Me and the ligand being identical to or different from those of (P), by bringing the precursor (P') into contact with the solid product resulting from stage (b), so as to graft the precursor (P') to the support by reaction of (P') with the remaining functional groups in the support, and optionally (d) treating the solid product resulting from stage (c) with hydrogen or a reducing agent capable of forming metal Me-hydrogen bonds, preferably by complete hydrogenolysis of the hydrocarbon ligands of the grafted precursor (P'), at a temperature in particular at most equal to the temperature T1 at which the metal compound is formed solely in the form (A) as defined above.

Stage (b) of the process can be carried out at a temperature such that most, preferably all, of the precursor (P) grafted to the support is converted into the metal compound in the form (B). The temperature during stage (b) can be chosen within the range from 460° C., preferably from 480° C., in particular from 500° C., up to a temperature lower than the sintering temperature of the support. Stage (d) is optional and can be carried out at a temperature equivalent to that of stage (b) of the first preparation process.

A fifth process for the preparation of a metal compound supported on and grafted to a solid support can comprise the following stages:

(a) grafting an organometallic precursor to the solid support under the same conditions as in stage (a) of the preceding preparation process, then (b) treating the solid product resulting from stage (a) under the same conditions as in stage (b) of the preceding preparation process, then (c) bringing the solid product resulting from stage (b) into contact with at least one compound Y capable of reacting with the metal Me of the form (A) and/or (B) prepared above, the contacting operation preferably being followed by removal of the unreacted compound Y and/or by a heat treatment at a temperature lower than the sintering temperature of the support, then (d) grafting to the solid product resulting from stage (c), an organometallic precursor (P'), identical to or different from (P), comprising the metal Me bonded to at least one hydrocarbon ligand, the metal Me and the ligand being identical to or different from those of (P), by bringing the precursor (P') into contact with the product resulting from stage (c), so as to graft the precursor (P') to the support by reaction of (P') with the remaining functional groups in the support, and optionally (e) treating the solid product resulting from stage (d) with hydrogen or a reducing agent capable of forming metal Me-hydrogen bonds, preferably by complete hydrogenolysis of the hydrocarbon ligands of the grafted precursor (P'), at a temperature in particular at most equal to the temperature T1 at which the metal compound is formed solely in the form (A) as defined above.

Stage (b) of the process can be carried out at a temperature equivalent to that of stage (b) of the fourth preparation process. In stage (c), the compound Y can be chosen from molecular oxygen, water, hydrogen sulphide, ammonia, an alcohol, in particular a $C_1$ to $C_{20}$, preferably $C_1$ to $C_{10}$, alcohol, a thiol, in particular a $C_1$ to $C_{20}$, preferably $C_1$ to $C_{10}$, thiol, a primary or secondary $C_1$ to $C_{20}$, preferably $C_1$ to $C_{10}$, amine, a molecular halogen, in particular molecular fluorine, chlorine or bromine, and a hydrogen halide, for example of formula HF, HCl or HBr. The heat treatment optionally carried out at the end of stage (c) can be carried out at a temperature ranging from 25 to 500° C. Stage (e) is optional and can be carried out at a temperature equivalent to that of stage (b) of the first preparation process.

In the processes for the preparation of a supported and grafted metal compound such as those described above, the operation of grafting to a solid support employs at least one organometallic precursor (P) or (P') comprising the metal Me bonded to at least one hydrocarbon ligand. The precursor can correspond to the general formula:

$$MeR''_a \qquad (4)$$

in which Me has the same definition as above, R" represents one or more identical or different and saturated or unsaturated hydrocarbon ligands, in particular aliphatic or alicyclic ligands, in particular $C_1$ to $C_{20}$, preferably $C_1$ to $C_{10}$, ligands having, for example, the same definition as that given above for the hydrocarbon radical, R, of the metal compound (C), and a is an integer equal to the degree of oxidation of the metal Me. The radical R" can be chosen from alkyly, alkylidene, alkylidyne, aryl, aralkyl, aralkylidene and aralkylidyne radicals. The metal Me can be bonded to one or more carbons of the hydrocarbon ligands, R", in particular via carbon-metal single, double or triple bonds, such as those connecting the metal Me to the hydrocarbon radical, R, in the metal compound (C).

In the processes for the preparation of a supported and grafted metal compound such as those described above, the solid support is preferably subjected beforehand to a dehydration and/or dehydroxylation heat-treatment, in particular at a temperature lower than the sintering temperature of the support, preferably at a temperature ranging from 200 to 1000° C., preferably from 300 to 800° C., for a period of time which can range from 1 to 48 hours, preferably from 5 to 24 hours. The temperature and the period of time can be chosen so as to create and/or to allow to remain, in the support and at predetermined concentrations, functional groups capable of grafting the precursor (P) or (P') by reaction. Mention may be made, among the functional groups known for the supports, of groups of formulae XH in which H represents a hydrogen atom and X corresponds to the same definition as given above for the support and in particular can represent an atom chosen from oxygen, sulphur and nitrogen. The most well-known functional group is the hydroxyl group.

The grafting operation in general can be carried out by sublimation or by bringing the precursor into contact in a liquid medium or in solution. In the case of sublimation, the precursor used in the solid state can be heated under vacuum and under temperature and pressure conditions which provide for its sublimation and its migration in the vapour state onto the support. The sublimation can be carried out at a temperature ranging from 20 to 300° C., in particular from 50 to 150° C., under vacuum.

It is also possible to carry out grafting by bringing into contact in a liquid medium or in solution. In this case, the precursor can be dissolved in an organic solvent, such as pentane or ethyl ether, so as to form a homogeneous solution, and the support can subsequently be suspended in the solution comprising the precursor or by any other method providing contact between the support and the precursor. The contacting operation can be carried out at ambient temperature (20° C.) or, more generally, at a a temperature ranging from −80° C. to +150° C. under an inert atmosphere such as nitrogen. If a portion of the precursor has not fixed to the support, it can be removed by washing or reverse sublimation.

The process of the present invention makes it possible to considerably improve the yield of the "methane-olysis" reaction resulting from bringing methane into contact with the starting alkane or alkanes (I) in the presence of the metal compound (C), the catalytic stability and activity of which over time are greatly enhanced by virtue of the application of a particularly high methane pressure.

The following examples illustrate the present invention and show the scale of the improvement in the reaction for the "methane-olysis" of alkanes.

EXAMPLE 1

Preparation of a Metal Compound (C) Based on Tantalum Hydride Supported on and Grafted to Silica A tantalum compound (C) supported on and grafted to silica was prepared in the following way.

In a first stage, 5 g of a silica, previously dehydrated and treated at 500° C., and then 20 ml of an n-pentane solution comprising 800 mg (1.72 millimol of tantalum) of tris (neopentyl)neopentylidenetantalum, used as precursor and corresponding to the general formula:

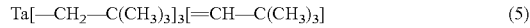
$$Ta[-CH_2-C(CH_3)_3]_3[=CH-C(CH_3)_3] \quad (5)$$

were introduced under an argon atmosphere into a glass reactor, which precursor, by reacting at 25° C. with the hydroxyl groups of the silica, was grafted to the silica. The excess unreacted precursor was removed by washing with n-pentane. The resulting solid compound, which constituted the organometallic compound grafted to the silica and which corresponded to the general formula:

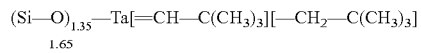
$$(Si-O)_{1.35}-Ta[=CH-C(CH_3)_3][-CH_2-C(CH_3)_3]$$
$$1.65$$

was then dried under vacuum.

In a second stage, the tantalum compound, thus supported on and grafted to the silica, was subsequently treated under an atmosphere 80 kPa of hydrogen at a temperature of 250° C. for 15 hours. By hydrogenolysis of the neopentyl and neopentylidene ligands, a tantalum compound (C) supported on and grafted to silica was formed which, per 100 parts by moles of tantalum, comprised:

72 parts by moles of a tantalum hydride grafted to the silica in the form (A) corresponding to the general formula:

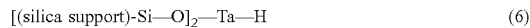
$$[(silica\ support)-Si-O]_2-Ta-H \quad (6)$$

and 28 parts by moles of a tantalum compound grafted to the silica in the form (B) corresponding the general formula:

$$[(silica\ support)-Si-O]_3-Ta \quad (7)$$

EXAMPLES 2 TO 5

Reaction of Methane with Propane (or "Methane-olysis" of Propane)

A mixture comprising, per $10^6$ mol of methane, $8 \times 10^2$ mol of propane was continuously passed, at a flow rate of 1.5 ml/min, successively under the following methane partial pressures: 0.0645 MPa (Comparative Example 2), 0.5 MPa (Example 3), 125 MPa (Example 4) and 5 MPa (Example 5), through a reactor with a capacity of 5 ml which was heated to 250° C. and which comprised 300 mg of the tantalum compound (C) prepared in Example 1 (59.3 micromol of active tantalum in the form (A)).

Bringing methane into contact with propane in the presence of the tantalum compound (C) resulted in the formation of ethane according to a propane "methane-olysis" reaction which is written according the following equation:

$$C_3H_8 + CH_4 \rightarrow 2C_2H_6 \quad (8)$$

For each example, the instantaneous percentage of conversion of the propane at various points in the reaction was measured and calculated, as was the number of moles of methane incorporated per mole of tantalum (in form (A)) after reacting for 3 600 minutes. The results of these measurements and calculations were collated in Table 1.

TABLE 1

| Example | Methane partial pressure (MPa) | % of conversion of the propane with reaction for 360 minutes | % of conversion of the propane with reaction for 3600 minutes | Number of mols of methane incorporated per mol of Ta after reacting for 3600 minutes |
|---|---|---|---|---|
| 2 (comparative) | 0.0645 | 10% | 0% | 0.01 |
| 3 | 0.5 | 98% | 16% | 0.19 |
| 4 | 1.25 | 99% | 62% | 1.58 |
| 5 | 5 | 99% | 91% | 2.67 |

Table 1 showed that the percentage of conversion of the propane in the propane "methane-olysis" reaction was greater in proportion and decreased less over time in proportion as the methane partial pressure applied increased. It was thus observed that the tantalum compound (C) had a catalytic activity which was remarkably stable over time, when the methane pressure applied to the "methane-olysis" reaction was high. In Example 5, it was found that the amount of butane formed was negligible so that the process carried out under these conditions essentially involved a propane "methane-olysis" reaction.

EXAMPLES 6 AND 7

Reaction of Methane with Propane at 250° C. and 300° C.

A propane "methane-olysis" reaction (Example 6) was carried out exactly as in Example 5, in particular at a temperature of 250° C., and another propane "methane-olysis" reaction (Example 7) was also carried out exactly as in Example 5, except the fact that the temperature of the reaction was 300° C. (instead of 250° C.).

In the reaction carried out at 250° C. (Example 6) it was observed that when 3 moles of propane were consumed per mole of tantalum, simultaneously 5.08 moles of ethane were produced. In the reaction carried out at 300° C. (Example 7), when 3 moles of propane were consumed at 300° C. per mole of tantalum, simultaneously 5.53 moles of ethane were produced.

These results showed that when a higher temperature was used in a "methane-olysis" reaction, ethane was produced in higher amounts.

EXAMPLE 8

Reaction of Methane with n-butane (or n-butane "Methane-olysis")

An n-butane "methane-olysis" reaction was carried out as in Example 5, except that, instead of passing a mixture of methane and propane into the reactor, a mixture comprising, per $10^6$ mol of methane, $5.3 \times 10^2$ mol of n-butane, with a methanol partial pressure equal to 5 MPa, was passed therein continuously.

It was observed that, under these conditions, the n-butane "methane-olysis" reaction resulted in the simultaneous formation of ethane and propane, that the percentage of conversion of the n-butane remained at a high value after a long reaction time and that the tantalum compound (C) deactivated relatively slowly over time.

EXAMPLE 9

Preparation of a Metal Compound (C) Based on Tungsten Hydride Supported on and Grafted to Silica A tungsten compound (C) supported on and grafted to silica was prepared precisely as in Example 1, except that, in the first stage, instead of using a solution of tris(neopentyl)neopentylidenetantalum in n-pentane as precursor, a solution of tris(neopentyl)neopentylidenetungsten in n-pentane, corresponding to the general formula:

$$W[-CH_2-C(CH_3)_3]_3[\equiv C-C(CH_3)_3] \quad (9)$$

was used and that, in the second stage, instead of carrying out the hydrogenolysis at 250° C., it was carried out at 150° C. A tungsten compound (C) supported on silica, essentially in the form (A) of a tungsten hydride, was thus obtained.

EXAMPLE 10

Reaction of Methane With Propane (or Propane "Methane-olysis")

A propane "methane-olysis" reaction was carried out as in Example 5, except that, instead of using the tantalum compound prepared in Example 1, the tungsten compound prepared in Example 8 was used.

It was observed that the "methane-olysis" reaction resulted in the formation of ethane, that the percentage of conversion of the propane remained at a high value after a long reaction time and that the tungsten compound deactivated relatively slowly over time.

EXAMPLES 11 AND 12

Reaction of Methane with Propane at 375° C. (or "Methane-olysis" of Propane)

A propane "methane-olysis" reaction (Example 11) was carried out exactly as in Example 5, except the fact that the temperature of the reaction was 375° C. (instead of 250° C.) and that the mixture of methane and propane continuously passed through the reactor comprised $10^4$ mol of propane per $10^6$ mol of methane.

A propane "methane-olysis" reaction (Example 12) was carried out exactly as in Example 5, except the fact that the temperature of the reaction was 375° C. (instead of 250° C.) and that the mixture of methane and propane continuously passed through the reactor comprised $10^5$ mol of propane per $10^6$ mol of methane.

In the two reactions, ethane was produced in great amounts.

The invention claimed is:

1. Process for the manufacture of alkanes comprising a catalytic reaction resulting from bringing methane into contact with at least one other starting alkane (I) in the presence of a metal compound (C) capable of catalysing a reaction for the splitting and/or recombination of a carbon-carbon bond and/or of a carbon-hydrogen bond and/or of a carbon-metal bond, which catalytic reaction results in the formation of at least one final alkane (II) having a number of carbon atoms equal to or greater than 2, which process comprises carrying out the contacting operation under a methane partial pressure equal to or greater than 0.1 MPa.

2. Process according to claim 1, wherein the methane partial pressure is chosen within a range from 0.1 to 100 MPa.

3. Process according to claim 1, wherein the contacting operation is carried out at a temperature ranging from −30° C. to +500° C.

4. Process according to claim 1, wherein the contacting operation is carried out in a molar ratio of methane to starting alkane(s) (I) ranging from 0.1:1 to $10^5$:1.

5. Process according to claim 4, wherein the contacting operation is carried out in a molar ratio of methane to starting alkane(s) (I) ranging from 60:1 to $10^5$:1.

6. Process according to claim 1, wherein it comprises contacting methane with a mixture of two or more starting alkanes (I).

7. Process according to claim 1, wherein the starting alkane (I) is either a substituted or unsubstituted acyclic alkane or a substituted cyclic alkane.

8. Process according to claim 7, wherein the starting alkane (I) is either a substituted or unsubstituted acylic alkane corresponding to the general formula:

$$C_nH_{2n+2}$$

in which n is an integer ranging from 2 to 60, or a substituted cyclic alkane corresponding to the general formula:

$$C_nH_{2n}$$

in which n is an integer ranging from 5 to 60.

9. Process according to claim 1, wherein the metal compound (C) comprises at least one metal atom, Me, selected from the group consisting of lanthanides, the actinides and the metals from Groups 2 to 12 of the Periodic Table of the Elements.

10. Process according to claim 9, wherein the metal atom, Me, is at least one metal selected from the group consisting of scandium, yttrium, lanthanum, titanium, zirconium, hafnium, vanadium, niobium, tantalum, chromium, molybdenum, tungsten, ruthenium, palladium platinum, iridium, cerium and neodymium.

11. Process according to claim 1, wherein the metal compound (C) is selected from the group consisting of metal compounds supported on and dispersed over a solid support, metal compounds supported on and grafted to a solid support, and non-supported metal compounds.

12. Process according to claim 11, wherein the supported and grafted metal compounds comprise a solid support to which are grafted one or more different or identical metal atoms, Me, bonded to the support via single or multiple bonds.

13. Process according to claim 12, wherein the metal atom, Me, supported on and grafted to the solid support, is bonded to at least one hydrogen atom and/or to at least one hydrocarbon radical via a carbon-metal single, double or triple bond.

14. Process according to claim 13, wherein the hydrocarbon radical is a saturated or unsaturated hydrocarbon radical having from 1 to 20.

15. Process according to claim 13, wherein the hydrocarbon radical is selected from the group consisting of alkyl, alkylidene, alkylidyne, aryl, aralkyl, aralkylidene and aralkylidyne radicals.

16. Process according to claim 1, wherein the metal compound (C) is selected from the group consisting of metal hydrides and organometallic compounds.

17. Process according to claim 11, wherein the metal atom, Me, of the supported and grafted metal compound has a degree of oxidation ranging from 1 to its maximum value.

18. Process according to claim 1, wherein it is carried out continuously.

19. Process according to claim 1, wherein the metal compound (C) is selected from the group consisting of metal hydrides and organometallic compounds of the metal Me, supported on and grafted to a solid support.

20. Process according to claim 1, wherein the methane partial pressure is within the range of 0.3 to 9.5 MPa.

21. Process for increasing the catalytic activity and stability of a metal compound (C) capable of catalysing a reaction for the splitting and/or recombination of a carbon-carbon bond and/or of a carbon-hydrogen bond and/or of a carbon-metal bond, which compound is employed in a catalytic reaction which results from bringing methane into contact with at least one other starting alkane (I) and which results in the formation of at least one final alkane (II) having a number of carbon atoms equal to or greater than 2, which process carrying out the contacting operation under a methane partial pressure equal to or greater than 0.1 MPa.

22. Process according to claim 21, wherein the methane partial pressure is within the range from 0.1 to 100 MPa.

23. Process according to claim 21, wherein the methane partial pressure is chosen within a range from 0.3 to 9.5 MPa.

* * * * *